United States Patent [19]
Yang et al.

[11] Patent Number: 5,803,925
[45] Date of Patent: Sep. 8, 1998

[54] IOL INSERTION APPARATUS WITH COVALENTLY BONDED LUBRICANT

[75] Inventors: Shih-Liang Stanley Yang, Laguna Hills; Crystal M. Cunanan, Mission Viejo; Thomas M. McNicholas, Laguna Niguel, all of Calif.

[73] Assignee: Allergan, Waco, Tex.

[21] Appl. No.: 769,324

[22] Filed: Dec. 19, 1996

Related U.S. Application Data

[63] Continuation-in-part of Ser. No. 373,822, Jan. 17, 1995, abandoned.

[51] Int. Cl.⁶ .................................. A61F 9/00; A61F 2/16
[52] U.S. Cl. ................................................ 606/107; 623/6
[58] Field of Search .......................... 606/1, 107; 623/4, 623/6; 604/172

[56] References Cited

U.S. PATENT DOCUMENTS

| | | |
|---|---|---|
| 4,681,102 | 7/1987 | Bartell . |
| 4,722,906 | 2/1988 | Guire . |
| 4,806,382 | 2/1989 | Goldberg et al. . |
| 4,973,493 | 11/1990 | Guire . |
| 4,979,959 | 12/1990 | Guire . |
| 5,073,166 | 12/1991 | Parks et al. . |
| 5,094,876 | 3/1992 | Goldberg et al. . |
| 5,098,619 | 3/1992 | Zelez . |
| 5,108,776 | 4/1992 | Goldberg et al. . |
| 5,130,160 | 7/1992 | Goldberg et al. . |
| 5,135,516 | 8/1992 | Sahatjian et al. . |
| 5,190,552 | 3/1993 | Kelman . |
| 5,217,492 | 6/1993 | Guire et al. . |
| 5,258,041 | 11/1993 | Guire et al. . |
| 5,263,992 | 11/1993 | Guire . |
| 5,290,548 | 3/1994 | Goldberg et al. . |
| 5,303,714 | 4/1994 | Abele et al. . |
| 5,331,027 | 7/1994 | Whitbourne . |
| 5,429,839 | 7/1995 | Graiver et al. . |
| 5,474,562 | 12/1995 | Orchowski et al. . |

FOREIGN PATENT DOCUMENTS

| | | |
|---|---|---|
| 0480809 | 4/1992 | European Pat. Off. . |
| 1936852 | 1/1970 | Germany . |
| 3610925 | 1/1987 | Germany . |
| 50-233131 | 3/1975 | Japan . |
| 61-009443 | 3/1986 | Japan . |
| 04215760 | 8/1992 | Japan . |
| 7900327 | 6/1979 | WIPO . |
| 9316176 | 8/1993 | WIPO . |
| 9420027 | 9/1994 | WIPO . |

*Primary Examiner*—Glenn K. Dawson
*Attorney, Agent, or Firm*—Frank J. Uxa

[57] ABSTRACT

Apparatus for inserting intraocular lenses (IOLs) into eyes are disclosed. In one embodiment, such apparatus includes a hollow tube including an interior wall defining a hollow space through which an IOL is passed and an outlet through which the IOL is passed from the hollow space into an eye, and a lubricity enhancing component covalently bonded to the hollow tube at the interior wall in an amount effective to at least assist in facilitating the passage of the IOL through the hollow space.

21 Claims, 3 Drawing Sheets

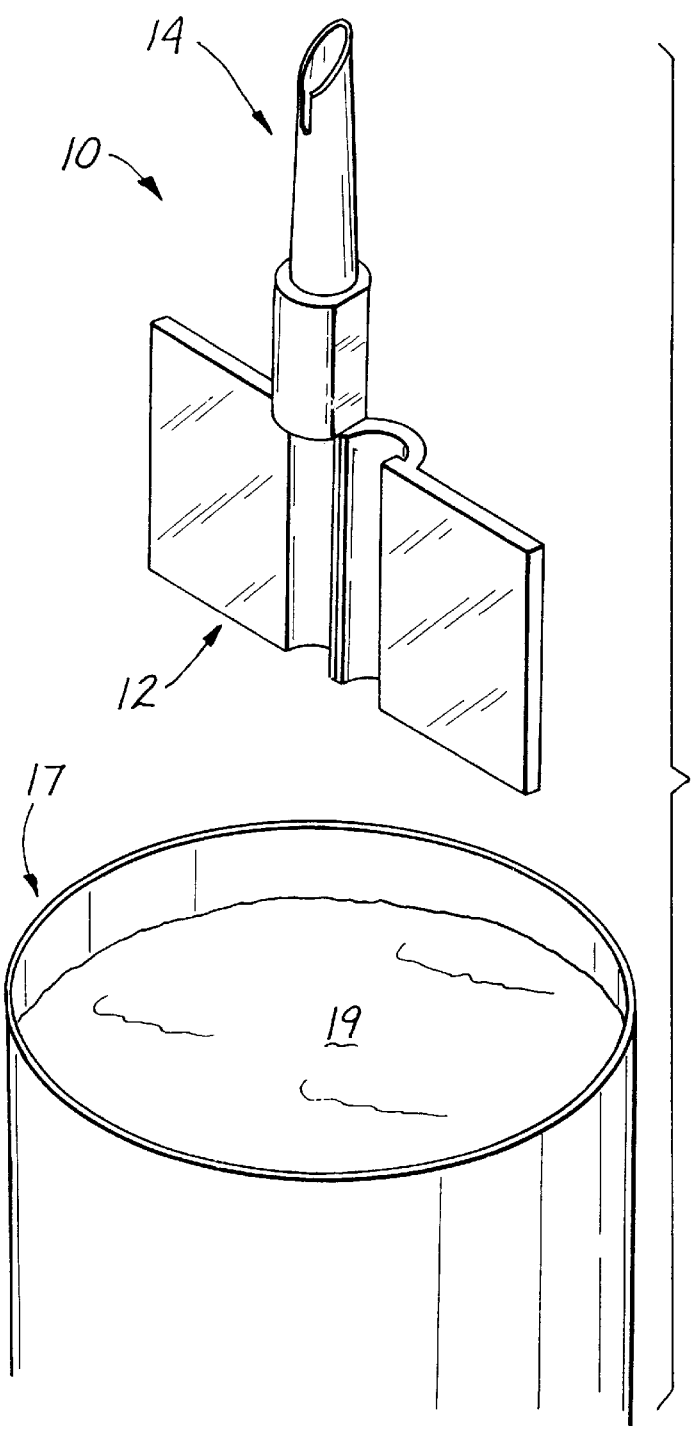
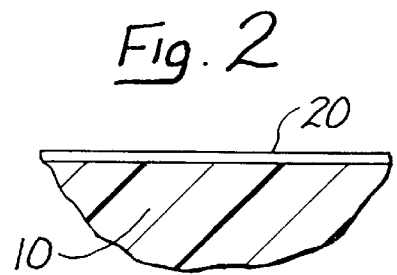

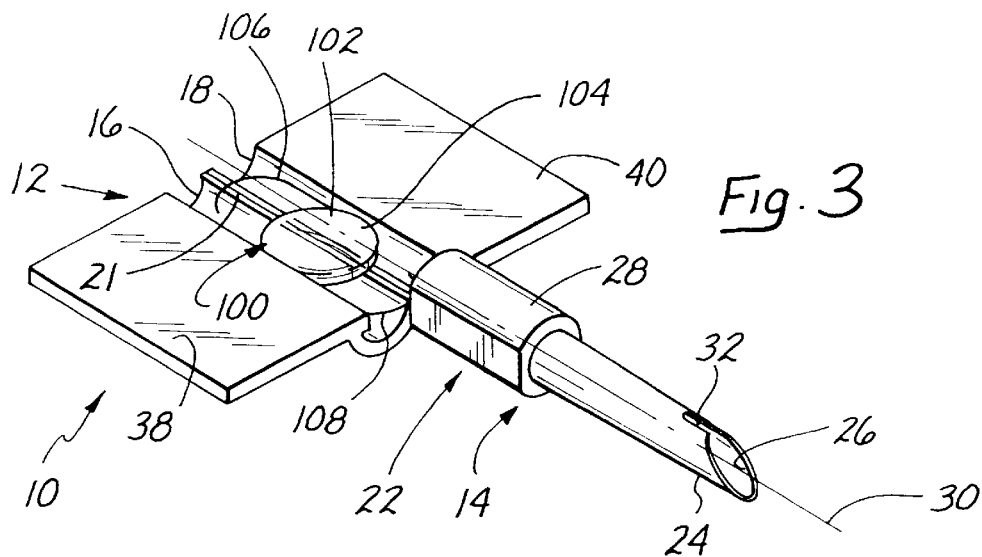
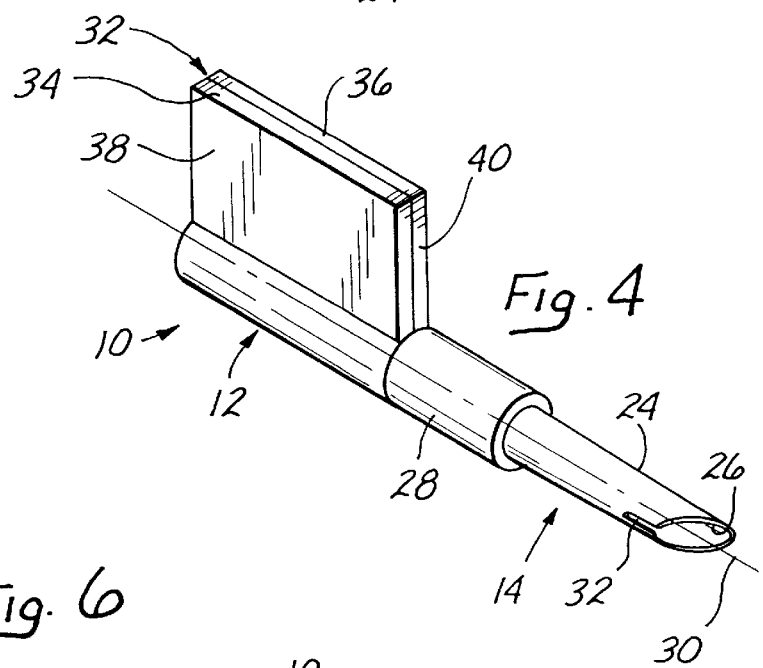
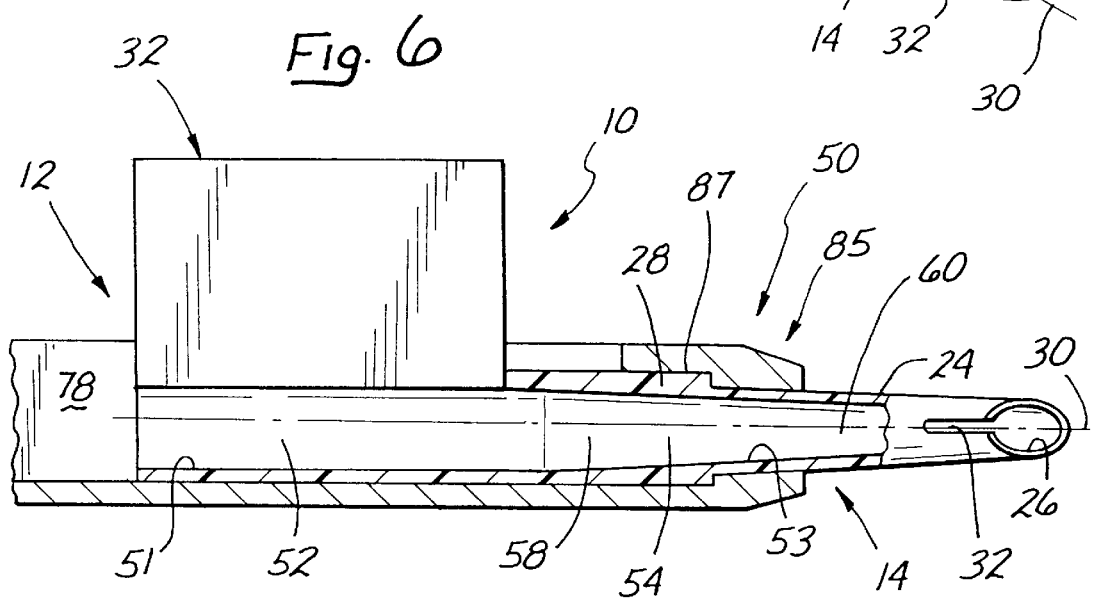

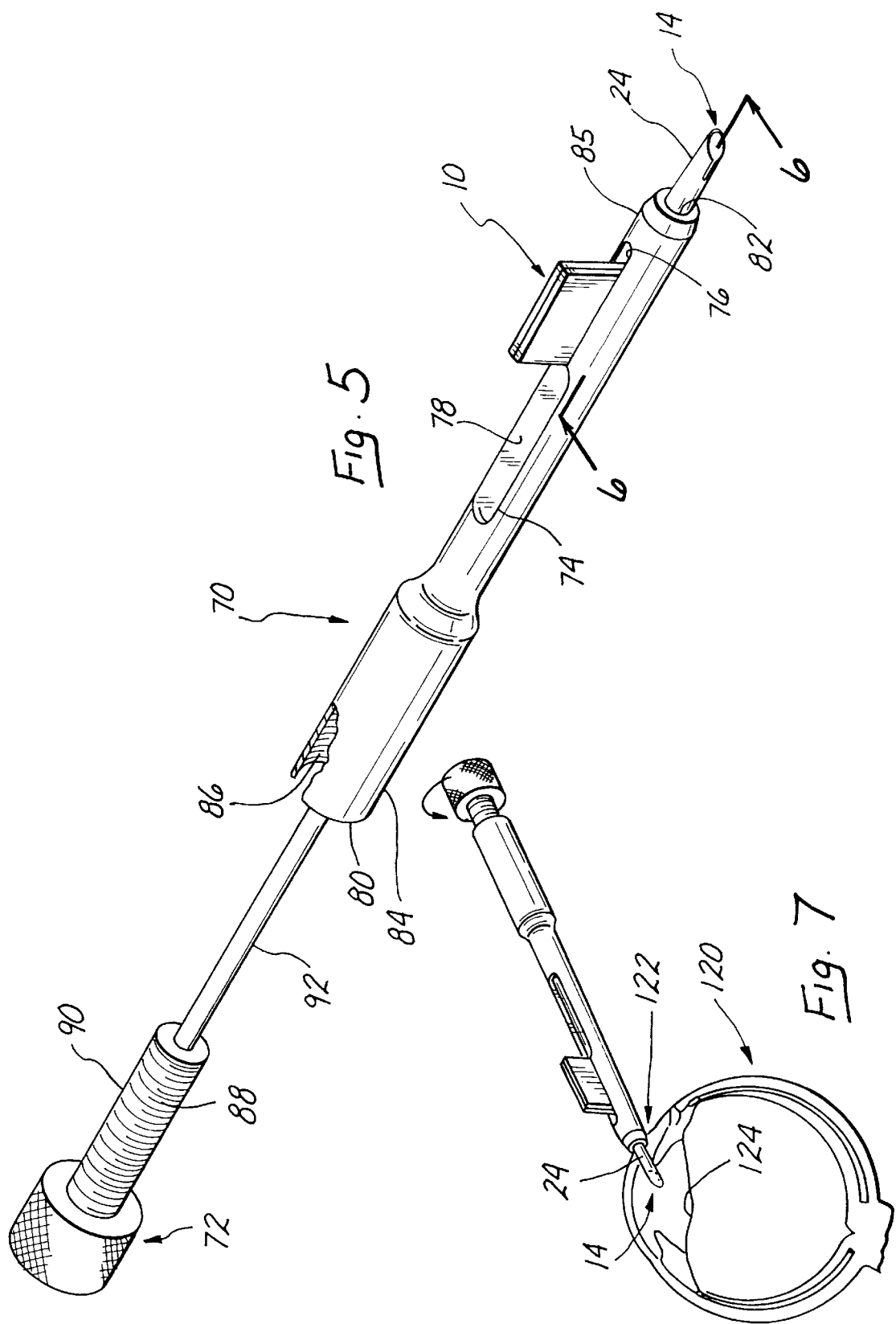

IOL INSERTION APPARATUS WITH COVALENTLY BONDED LUBRICANT

RELATED APPLICATION

This application is a continuation-in-part of application Ser. No. 08/373,822, filed Jan. 17, 1995, now abandoned.

BACKGROUND OF THE INVENTION

The present invention relates to apparatus for inserting an intraocular lens through a small incision into an eye and to methods for inserting an intraocular lens into an eye. More particularly, the invention relates to a modified apparatus for inserting a foldable intraocular lens into an eye and to methods using such modified apparatus to insert a foldable intraocular lens into an eye.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic which extends from the optic and becomes affixed in the eye to secure the lens in position. The optic normally includes an optically clear lens. Implantation of such IOLs into the eye involves making an incision in the eye. It is advantageous, to reduce trauma and speed healing, to have an incision size as small as possible.

IOLs are known which are foldable (deformable) so that the IOL can be inserted through a smaller incision into the eye. A substantial number of instruments have been proposed to aid in inserting such a foldable lens in the eye.

Many of the prior art IOL insertion systems load and/or fold the lens at the distal end, that is at the end closest to the eye or the end inserted into the eye. Such "distal loading" systems often disadvantageously include a space consuming loading component at or near the distal end of the system which causes the distal end to be relatively large. This relatively large distal end makes inserting the IOL through a small incision more difficult, if not impossible. Systems which fold and load the IOL proximally of the distal end provide certain advantages, such as reduced stress on the IOL and/or inserter, relative to "distal loading" systems.

However, whether using a distal loading or proximal loading system, one factor which limits the size of the inserter tube involves the inserter tube itself. For example, the material from which the inserter tube is made, for example, polypropylene and the like polymeric materials, may not be compatible for allowing optics, for example, made from silicone polymeric materials, to pass through relatively small hollow spaces. For example, the injector tubes may be made of materials, in particular polymeric materials, which are relatively hydrophobic and/or have insufficient lubricity to facilitate the passage of a folded IOL through the tube.

As a result of this incompatibility or lack of lubricity, the hollow space of the injector tube must be made relatively larger to accommodate the folded intraocular lens. This is detriment since, as noted above, it is advantageous to have the smallest possible incision for insertion of the IOL. In addition, if one were to use a small diameter tube to pass the IOL, excessive force might be needed to pass the IOL through the small hollow space thereby increasing the risks of damaging the IOL.

One approach that may be considered is to use a lubricity agent in passing the IOL through the insertion apparatus. For example, Orchowski et al U.S. Pat. No. 5,474,562 discloses the use of visco elastic liquid solutions and/or balanced salt liquid solutions to lubricate the passage of an IOL through an inserter. However, such lubricity agents have been found to be substantially ineffective when used with IOLs made of certain materials which exhibit relatively large friction against the inserter tube, for example, certain silicone materials, or when the injector size is at or less than 3.5 mm (for 3.5 mm incision). It would be advantageous to provide a system for inserting IOLs which are more universally effective.

Graiver et al U.S. Pat. No. 5,429,839 discloses coating the outside or exterior surface of a catheter or medical tube with covalently bonded hydrophilic polymers to increase lubricity and to reduce the adsorption of proteins and the adhesion of blood platelets on the outside surface of the catheter or tube as the catheter or tube is passed into a patient's body. This patent discloses coating the outside surfaces of catheters to increase biocompatiblity by reducing the interaction between the intruding catheters, the vein tissue and blood components. This is different than an IOL inserter which involves interactions between the IOL and inserter surfaces. In short, this patent discloses or suggests nothing regarding passing IOLs through inserters.

It would be advantageous to provide an IOL insertion apparatus and method for using same which has wide applicability and facilitates the passage of an IOL through the apparatus in a controlled manner without using excessive force.

SUMMARY OF THE INVENTION

New apparatus for injecting IOLs and methods for using such apparatus have been discovered. The present apparatus achieve enhanced lubricity, thus providing for controlled insertion of an IOL into an eye, for example, for the use of effective, reliable and non-excessive amounts of force to inject a folded IOL into an eye. The present system provides for controlled, reliable, easy and convenient insertion of IOLs, including those which exhibit relatively large or high friction against the inserter. In addition, the present invention provides for inserting folded IOLs through very small incisions in the eye. The present invention is straightforward, easy to practice, and involves little or no modification of surgical techniques. The methods included in the present invention are straightforward and easy to practice, and often involve surgical techniques which are well practiced and conventionally used to insert IOLs into eyes.

In general, the present invention involves apparatus for inserting IOLs into an eye which include a lubricity enhancing component covalently bonded to the apparatus, for example, at the interior wall defining a hollow space through which an IOL is passed, to at least assist in facilitating the passage of the IOLs through the apparatus. Covalent attachment or bonding of such lubricity enhancing components is particularly effective since the amount of such component present, and therefore, at least to some extent, the degree of enhanced lubricity, is conveniently controlled and stable on a long term basis, for example, has a long term shelf life. In addition, there is reduced chance or risk of the lubricity enhancing component being disadvantageously removed from the surface of the apparatus as the IOL passes through the apparatus into the eye.

The use of the present covalently bonded lubricity enhancing components allows successful injection of foldable IOLs, such as silicone-based IOLs, foldable acrylic-based IOLs and the like, including those which exhibit relatively large friction against the inserter, for example, employing inserters made of polypropylene and the like polymeric materials, through incisions about 3.5 mm or less, preferably about 3.0 mm or about 2.8 mm or less, and still more preferably less than 2.8 mm.

In one broad aspect of the present invention, apparatus for inserting an IOL through a small incision into the eye are provided. Such apparatus comprise a hollow tube including an interior wall defining a hollow space through which an IOL is passed and an outlet or end opening through which the IOL is passed from the hollow space into an eye. A lubricity enhancing component is covalently bonded to the hollow tube at the interior wall in an amount effective to at least assist in facilitating the passage of the IOL through the hollow space. The lubricity enhancing component may be covalently bonded to the hollow tube using methods known in the art, such as plasma and/or other activation of the tube to form functional groups that are chemically bondable to functional groups on the precursors to the lubricity enhancing components, and employing a difunctional or multifunctional linking component which is effective to react with both the tube and the lubricity enhancing component precursor. Other methods may be employed to covalently bond the lubricity enhancing component to the hollow tube.

In a particularly useful embodiment, the covalently bonded lubricity enhancing component is effective to reduce the force needed to pass the IOL through the hollow space of the tube relative to the force needed to pass an identical IOL through the hollow space of a similar apparatus without the lubricity enhancing component. This "reduced force" feature of the present invention is particularly useful, even when no reduction in the size of the incision is obtained. The use of reduced force allows the surgeon to have still more control of the rate at which the IOL is inserted into the eye and, in addition, reduces the risk of damage to the eye during IOL insertion.

The hollow tube is preferably made of a polymeric material, more preferably selected from polypropylene and the like materials.

The lubricity enhancing component is preferably selected from the group consisting of hydrophilic components, oleophilic components and mixtures thereof.

In one useful embodiment, the present apparatus further comprises a loading portion sized and adapted to receive an IOL for passage into the hollow space. The lubricity enhancing component is preferably covalently bonded to the loading portion in an amount effective to at least assist in facilitating the passage of the IOL into the hollow space. Thus, both the hollow tube and the loading portion include effective amounts of the lubricity enhancing component to at least assist in facilitating passage of the IOL from the loading portion into the hollow tube and from the hollow tube into the eye. In addition, it is more convenient to treat both the hollow tube and loading portion, which together are preferably a single, integrally formed unit, with the lubricity enhancing component, rather than treating only the hollow tube with such component.

The loading portion is preferably sized and adapted to receive an IOL, for example, in an unfolded state, and to hold the IOL in a folded state. The loading portion can be structured to at least facilitate the folding of the IOL from the unfolded state to a folded state. The hollow tube includes an interior wall which defines a hollow space preferably sized to receive the IOL in a folded state from the loading portion and to pass the folded IOL to an open outlet through which the IOL is passed into an eye.

Methods for inserting an IOL into an eye are also provided and are included within the scope of the present invention. In one embodiment, such methods comprise placing an outlet or end opening of a hollow tube in or in proximity to an incision in an eye, and passing an IOL from the hollow tube through the outlet or opening into the eye. The hollow tube includes an interior wall defining a hollow space containing an IOL in a folded state and an effective amount of a liquid component, preferably a liquid aqueous component. A lubricity enhancing component is provided and is covalently bonded to the hollow tube at or near the interior wall. The liquid component and the lubricity enhancing component together are present in an amount effective to facilitate passing the IOL in a folded state through the hollow space. Preferably, the lubricity enhancing component is effective to reduce the force needed to pass the IOL in a folded state through the hollow space relative to the force needed to pass an identical IOL in a folded state through the hollow space of a similar apparatus without the lubricity enhancing component. In a particularly useful embodiment, the hollow tube is made of a polymeric material, such as polypropylene and the like polymeric materials, and the IOL comprises an optic including a silicone polymeric material, a deformable acrylic-based polymeric material and the like. Examples of useful liquid components includes liquid aqueous components, such as liquid aqueous salt solutions, liquid aqueous media containing visco elastic components, mixtures thereof and the like.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 1 is an schematic illustration showing an IOL inserter in accordance with the present invention being treated to form a covalently bonded lubricity enhancing component thereon.

FIG. 2 is a fragmentary illustration of a small portion of the IOL inserter shown in FIG. 1 after having been treated to form a lubricity enhancing component thereon.

FIG. 3 is a front side view, in perspective, of an apparatus in accordance with the present invention with the load chamber in the open position.

FIG. 4 is a side view, in perspective, of the apparatus shown in FIG. 3 with the load chamber in the closed position.

FIG. 5 is a front side view, in perspective, of the apparatus shown in FIG. 4 loaded into a hand piece.

FIG. 6 is a side view, partly in cross-section, taken generally along line 6—6 of FIG. 5.

FIG. 7 is a somewhat schematic illustration showing the apparatus shown in FIG. 5, with the hand piece partially in cross-section, being used to insert an IOL into an eye.

DETAILED DESCRIPTION OF THE DRAWINGS

FIG. 1 illustrates an IOL inserter, shown generally at 10, including a load chamber 12 and an injection tube 14. In FIG. 1, the IOL inserter 10, which is made of polypropylene, is shown about to be immersed in a bath 16 of a precursor of a hydrophilic component 19, such as polyethylene glycol. Preferably, only the interior surfaces of the IOL inserter 10 are treated with the precursor. This selective application of the precursor can be achieved in any suitable manner, such as by spraying, brushing, irrigating and the like. The purpose of treating IOL inserter 10 with the hydrophilic component precursor 19 is to covalently bond all of the exposed interior surfaces of IOL inserter 10 with a hydrophilic component which enhances the lubricity of IOL inserter 10, for example, of the lumens defined by load chamber 12 and injection tube 14 to at least assist in facilitating the passage of an IOL therethrough.

Forming a covalently bonded hydrophilic component on the exposed surfaces of IOL inserter 10 can be accomplished in any one of a number of ways. Examples of forming such covalently bonded coatings include those set forth in the following: Guire U.S. Pat. No. 4,979,959; Guire U.S. Pat. No. 5,263,992; Guire U.S. Pat. No. 4,722,906; Guire et al U.S. Pat. No. 5,217,492; Guire et al U.S. Pat. No. 5,258,041; and Swan et al U.S. Pat. No. 5,414,075, the disclosures of each of which is incorporated in its entirety herein by reference.

One useful method of covalently bonding a hydrophilic component, such as polyethylene glycol residue, to IOL inserter 10 is as follows. A quantity of polyethylene glycol of appropriate molecular weight, for example, about 1000, is reacted with a moiety to form a compound having the formula $$A—PEG$$

wherein A is a reactive group, for example, selected from a photochemically reactive group or other type of reactive group, capable in response to specific activation of bonding covalently to the surfaces of IOL inserter 10; and PEG is the residue of the original polyethylene glycol employed, and includes substantially all of the hydrophilic properties or characteristics of this original material.

Examples of photochemically reactive groups may be typified by aryl, alkyl and acyl azides, oxazidines, isocyanates (nitrene generators), alkyl and 2-ketodiazo derivatives and diazirines (carbene generators), aromatic ketones (triplet oxygen generators), aromatic diazonium derivatives and numerous classes of carbonium ion and radical generators. Reference is made to Frederick J. Darfler and Andrew M. Tometsko, chapter 2 of *Chemistry and Biochemistry of Amino Acids, Peptides and Proteins* (Boris Weinstein, ed) vol. 5, Marcel Dekker, Inc. New York, 1978, for further description of photochemically reactive groups.

The compound, that is A—PEG, thus formed is applied to the exposed surface, preferably only to the interior surface, of IOL inserter 10, for example, by applying a solution containing the compound to such surface. The resulting coated IOL inserter 10 is then subjected to the photactivation energy, e.g., light, and/or the like, effective to cause the group A to react with the IOL inserter at conditions effective to covalently bond the residue of the compound, A-PEG, to the IOL inserter. As shown in FIG. 2, IOL inserter 10, after the above-noted processing, includes a hydrophilic coating 20 of the compound A—PEG residue on the surfaces.

In another method of covalently bonding a lubricity enhancing component to an IOL inserter, the IOL inserter is pre-treated, for example, with plasma, to prime the exposed surfaces thereof so that such exposed surfaces are more susceptible to being wetted by the solution of the lubricity enhancing component precursor. After the IOL inserter is primed by the plasma, the IOL inserter is exposed to the coating solution for a period of time so that substantially all of the exposed interior surfaces of the IOL inserter are completely wetted with the precursor. At this point, the IOL inserter 10 is placed at conditions, for example, exposed to effective light energy, to facilitate the photo reaction of the lubricity enhancing component precursor with the exposed surfaces. Once this reaction has occurred, the IOL inserter includes a coating of the lubricity enhancing component on all exposed surfaces thereof.

An additional method of covalently bonding the lubricity enhancing component to an IOL inserter involves using a combination of a multifunctional component or reagent and ultraviolet (UV) light or radiation. In general, a multifunctional component, that is a component that has groups which react with both the IOL inserter material and with the lubricity enhancing component precursor, is applied to the interior surface of the IOL inserter. This coated IOL inserter is exposed to UV radiation in order to promote covalent bond formation at the interior surface of the inserter. After washing to remove the unbound multifunctional component, the precursor of the lubricity enhancing component to be covalently bonded is applied to the interior surface of the IOL inserter. A second exposure to UV radiation is effective to form the covalently bonded lubricity enhancing component at the interior wall of the IOL inserter. A particularly useful multifunctional reagent is tetrakis(4-benzoylbenzoate ester) of pentaerythritol, for example, when used with precursors such as polyvinylpyrrolidone and the like. This methodology is described in detail in Swan U.S. Pat. No. 5,414,075.

A further method of covalently bonding a lubricity enhancing component to an IOL inserter involves the use of gamma ray and/or election beam irradiation to induce graft polymerization. In general, an IOL inserter is immersed in a monomer (for example, a compound from which a hydrophilic polymeric component is derived) or a solution containing a monomer. The immersed IOL inserter is then subjected to gamma ray and/or election beam irradiation to induce graft polymerization of the monomer onto the surface of the IOL inserter. The use of gamma ray and/or election beam irradiation to induce graft polymerization is more fully described in Goldberg et al U.S. Pat. No. 4,806,382; Goldberg et al U.S. Pat. No. 5,094,876; Goldberg et al U.S. Pat. No. 5,108,776; Goldberg et al U.S. Pat. No. 5,130,160; and Goldberg et al U.S. Pat. No. 5,290,548, the disclosures of each of which is incorporated in its entirety herein by reference. Each of these patents is directed to providing biocompatibility and does not teach or suggest enhancing lubricity or IOL inserters.

The lubricity enhancing component is preferably covalently bonded to the IOL inserter without employing gamma ray or electron beam irradiation. Sources of gamma ray and election beam irradiation are relatively expensive and bulky so that it is relatively difficult to use such irradiation at the facility where the IOL inserters are produced. In addition, subjecting the IOL inserter immersed in a monomer-containing solution to gamma or election beam irradiation may result in a graft polymeric coating which is substantially thicker than desired. This can lead to an additional and disadvantageous processing step in which excess coating material is removed. In view of these problems, it is preferred to employ other methods to provide an IOL inserter with a covalently bonded lubricity enhancing component.

The lubricity enhancing components useful in the present invention may be selected from suitable components which function as such lubricity enhancing components as described herein. The lubricity enhancing component is present in an amount effective to enhance the lubricity of the interior wall of the hollow tube defining a hollow space through which the IOL passes in being inserted into the eye.

Such lubricity enhancing components are preferably effective to provide such enhanced lubricity for relatively long periods of time, for example, for at least about 3 months or at least about 6 months, and preferably about 1 year or more, so that the IOL inserter has a relatively long shelf life and can be used after being packaged and stored for such relatively long periods of time and still obtain the substantial enhanced lubricity benefits.

The covalent bonding of the lubricity enhancing component to the IOL inserter is preferably effective to maintain this component secured to the inserter as the IOL is inserted into the eye. In other words, it is preferred that such covalent bonding is effective to substantially prevent the lubricity enhancing component from sloughing off as the IOL is inserted into the eye. Thus, the present invention conveniently provides for enhanced lubricity and ease of inserting an IOL into an eye while, at the same time, reducing, or even eliminating, sloughing off of the lubricity enhancing component.

Particularly useful lubricity enhancing components include those selected from hydrophilic components, oleophilic components and mixtures thereof. Examples of hydrophilic lubricity enhancing components include, but are not limited to, those derived from polyethylene glycol, polyvinylpyrrolidone, poly (N-vinyl lactams), polyacrylic acid, polyethylene oxide, polypropylene oxide, polyvinyl pyridine, polyvinyl alcohol, polysaccharides, polycarboxyl methyl cellulose, polymethacrylic acid, polyacrylamide, polypeptides, poly sodium styrene sulfonate, polyhydroxyethyl methacrylate, heparin and the like and mixtures thereof. If a hydrophilic lubricity enhancing component is employed, it is preferred that the IOL inserter be immersed or otherwise contacted with water, for example, a saline solution, to hydrate the hydrophilic component. Such hydration is effective to facilitate the lubricity enhancing characteristics of the hydrophilic component.

Lubricity enhancing components which are not significantly hydratable by an isotonic aqueous liquid at room temperature may be considered oleophilic lubricity enhancing components. Examples of useful oleophilic lubricity enhancing components include, but are not limited to, those derived from carboxylic acids having about 10 to about 30, carbon atoms per molecule, glycerol monostearate, glycerol monopalmitate, glycerol monooleate and the like and mixtures thereof.

It should be noted that, because of the covalent bonding involved in the present invention, the lubricity enhancing components identified herein are often present in a slightly altered form relative to the more commonly known precursors or forms of such components. However, such lubricity enhancing components often have substantially the same or better lubricity enhancing properties relative to the corresponding precursors or forms and, in addition, have the added advantage of being covalently bonded to the IOL inserter.

FIGS. 3 to 7 illustrate the use of IOL inserter 10 including a coating of lubricity enhancing component 20 on all exposed interior surfaces thereof. IOL inserter 10 is merely illustrative of the inserters included within the scope of the present invention. Inserters including the covalently bonded lubricity enhancing components described herein and having configurations substantially different from IOL inserter 10 are included within the scope of the present invention.

The body of IOL inserter 10 (that is other than coating 20) is an integrally formed, for example, molded, unit made of propropylene. Load chamber 12 includes a first member 16 and a second member 18 which are secured or joined together and are hingeably moveable relative to each other along line 21, which is parallel to the longitudinal axis 30 of inserter 10.

Injection tube 14 includes a proximal end portion 22, a distal end portion 24 and an open distal end 26. A reinforcing collar 28 is coincidental with the proximal end portion 22 of injection tube 14. Injection tube 14 also includes a through slot 32.

As shown in FIG. 3, inserter 10 is in the opened position. In contrast, in FIG. 4, inserter 10 is shown in the closed position. In the closed position, the load chamber 12 includes a top 32 which is a combination of top surfaces 34 and 36 of first wing 38 and second wing 40, respectively, of first member 16 and second member 18, respectively. First and second wings 38 and 40 are effective for a human user of inserter 10 to hold and manipulate the inserter 10 while using it, as described hereinafter.

Inserter 10 is described in more detail with reference to FIG. 5, which shows the inserter in combination with hand piece 70. When used in combination with hand piece 70, the load chamber 12 of inserter 10 is in the closed position, as shown in FIG. 4.

Referring to FIG. 6, with load chamber 12 in the closed position, the load chamber includes an interior wall 51 which defines a first lumen 52 that is elongated in a direction parallel to the longitudinal axis 30 of inserter 10. Injection tube 14 includes a tapering interior wall 53 which defines a distally tapering second lumen 54.

The first lumen 52 is aligned with the second lumen 54 so that a folded IOL in the first lumen can be passed directly from the first lumen into the second lumen. The taper of proximal portion 58 of second lumen 54 is more severe than the slight taper which exists in the distal portion 60 of the second lumen. The more severe taper in the proximal portion 58 is effective to further fold the IOL as the IOL is passed into the second lumen 54. This further folding is advantageous because the further folded IOL can be inserted into the eye through a smaller incision. The enhanced lubricity resulting from the coating 20 facilitates this further folding so that a reduced amount of force is required to further fold the IOL and/or the degree of further holding of the IOL can be increased so that ultimately, the IOL can be inserted through an even smaller incision. The coating 20 also advantageously reduces the risk of tearing and/or otherwise damaging the IOL as the IOL is passed through the first lumen 52 and second lumen 54.

With reference to FIG. 5, inserter 10 is shown in combination with hand piece 70 and push rod member 72. Hand piece 70 includes a relatively large, elongated first through opening 74 and a relatively small, elongated second through opening 76. Hand piece 70 includes a through bore 78 which extends from the proximal end 80 to the distal end 82 of the hand piece. The proximal end portion 84 of hand piece 70 includes threads 86 which are adapted to engage and mate with threads 88 of the proximal segment 90 of push rod member 72. Rod element 92 of push rod member 72 is adapted to pass through bore 78, first lumen 52, second lumen 54 and out of open distal end 26. Hand piece 70 and push rod member 72 are made of metal, such as surgical grade stainless steel or the like metals. The distal end portion of rod member 72 can be made of a soft polymeric material, for example, configured to be introduced into and held in a fold of a folded IOL as the IOL is passed through the inserter.

Inserter 10 is operated and functions as follows. When it is desired to load an IOL into inserter 10, the inserter is placed, for example, manually placed, in a configuration as shown in FIG. 3. With load chamber 12 in the opened position, a quantity, for example, on the order of about 0.01 to about 0.2 or about 0.5 ml, of a liquid component is placed in the troughs formed by the first and second members 16 and 18 and throughout the injection tube. This liquid component preferably is ophthalmically acceptable, and effective, together with the covalently bonded lubricity enhancing component, in facilitating the passage of the IOL through the inserter 10. Although any suitable liquid component may be employed, particularly useful are liquid aqueous components. Examples include liquid aqueous salt solutions, such as commercially available balanced salt solutions; liquid aqueous media including visco elastic components, such as hyaluronate alkali metal salts, hydroxypropylmethyl cellulose, other water soluble cellulose derivatives, condroitin sulfate, mixtures thereof and the like.

After the liquid component has been provided, an IOL, such as shown generally at 100, is placed, for example, using forceps, in between first and second members 16 and 18. This placement is such that the anterior face 102 of optic 104 faces upwardly, as shown in FIG. 3. The optic 104 is made of a silicone polymeric material. The filament haptics 106 and 108 of IOL 100 are located as shown in FIG. 3, so that the fixation members are located generally parallel to, rather than transverse to, the longitudinal axis 30.

With IOL 100 placed as shown in FIG. 3, first and second members 16 and 18 are hingeably moved relative to each other, for example, by manually bringing first and second wings 38 and 40 together, to place the load chamber 12 in the closed position, as shown in FIG. 4. With load chamber 12 in the closed position, IOL 100 is in a folded state, that is optic 104 is folded. The relative movement of first and second members 16 and 18 to move the load chamber from the open position to the closed position is effective to fold the lens. The folded IOL 100 is now located in the first lumen 52. For clarity sake, the folded IOL is not shown in any of FIGS. 4, 5, 6 or 7.

With the inserter 10 configured as shown in FIG. 4 and folded IOL 100 located in first lumen 52, the inserter 10 is placed in association with hand piece 70, as shown in FIG. 5. In this configuration, the distal end portion 24 of injection tube 14 extends distally beyond the distal end 82 of hand piece 70. As shown in FIG. 6, the distal portion 85 of hand piece 70 includes an inner wall 87 which is configured to receive reinforcing collar 28 in abutting relation.

With inserter 10 so placed relative to hand piece 70, push rod member 72 is pushed into the through bore 78 and into the inserter 10 to push the IOL 100 from the first lumen 52 into the second lumen 54. As the threads 88 come in contact with and engage threads 86, the push rod member 72 is rotated, as shown in FIG. 7, so as to thread the push rod member onto the proximal end portion 84 of hand piece 70. By gradually moving push rod element 92 through bore 78 of hand piece 70, the folded IOL 100 is urged to move from first lumen 52 into second lumen 54, through open distal end 26 and into the eye.

Referring now to FIG. 7, the IOL 100 is to be placed in eye 120 into an area formerly occupied by the natural lens of the eye. FIG. 7 shows the sclera 122 having an incision through which the distal end portion 24 of injection tube 14 is passed. Alternately, the incision can be made through the cornea. Distal end portion 24 has a sufficiently small cross-section to pass into the eye 120 through an incision in the sclera 122.

The injection tube 14 is manipulated within eye 122 until it is positioned so that IOL 100 can be properly positioned in eye 122, that is in the anterior chamber, the posterior chamber, the capsular bag 124 or in the sulcus, after being released. Thus, the surgeon is able to controllably position the distal end portion 24 of injection tube 14, with IOL 100 in the first lumen 52 of load chamber 12. Once distal end portion 24 is so positioned, the rod element 92 is urged distally, by rotating (threading) push rod member 72 onto hand piece 70, to pass the IOL 100 into and through the second lumen 54, through the open distal end 26 of injection tube 14 and into the eye 120. The anterior face 102 of IOL 100 faces generally forwardly in the eye 120 as the IOL is released from the inserter 10. In other words, the IOL 100 passes through first lumen 52, second lumen 54 and open distal end 26 and into eye 120 without flipping or otherwise becoming mispositioned. Only a relatively small amount of, if any, post-insertion re-positioning is needed to properly position IOL 100 in eye 120.

After the IOL 100 has been inserted into the eye, the rod element 92 is moved proximally into the injection tube 14 and the distal end portion 24 of the injection tube is removed from the eye. If needed, the IOL 100 can be repositioned in the eye by a small, bent needle or similar tool inserted into the same incision.

Once the IOL 100 is properly positioned in eye 120 and inserter 10 is withdrawn from the eye, the incision in the sclera may be mended, for example, using conventional techniques. After use, inserter 10 is preferably disposed of. Hand piece 70 and push rod member 72 can be reused, after sterilization/disinfection.

The following non-limiting examples illustrate certain aspects of the present invention.

EXAMPLE 1

Ten (10) cartridges, having a structure similar to that of the body of IOL inserter 10, made of PD701NW polypropylene (Himont USA Inc.) are selected. These cartridges, which have an injection tube with a distal end suitable for insertion into an approximately 2.6 mm incision, are treated to form a coating of polyvinylpyrrolidone covalently bonded at the interior walls of the cartridges. These coatings can be provided using any suitable technique or combination of techniques.

Swan et al U.S. Pat. No. 5,414,075 discloses methods useful to provide such coatings. Thus, a multifunctional reagent, such as tetrakis(4-benzoylbenzoate ester) of pentaerythritol (hereinafter TBP) is applied to the interior surface of a clean cartridge. This is accomplished by applying, for example, spraying, irrigating or brushing, a coating of a solution of TBP in isopropyl alcohol on the interior surface. The TBP-coated surface is then exposed to ultraviolet light in order to cause covalent bond formation between TBP and the interior surface of the cartridge.

After washing to remove unbound TBP, the interior surface of the cartridge is coated with an aqueous (deionized water) solution of polyvinylpyrrolidone (hereinafter PVP). The PVP-coated surface is exposed to ultraviolet light to covalently bond the PVP to the interior surface.

A series of tests are run using these treated cartridges. Each of these tests is conducted as follows. With the load chamber in the open position, about 0.02 to 0.2 ml of a visco elastic agent, that is an aqueous balanced salt solution of sodium hyaluronate sold by Allergan, Inc. under the trademark Vitrax, is injected into the injection tube and along the bottom of both sides of the troughs formed by the first and second wings.

A three-piece IOL, sold under the trademark SI-40 by Allergan Medical Optics, is placed, anterior side up, between the first and second wings. The first and second wings are then closed to approximately a 45° angle. Using rounded blade forceps the edges of the optic of the IOL are pushed down into the tube portion of the wings, and the center of the optic is pushed down as the wings were closed further. After closing the wings, the cartridge is placed in association with a hand piece, as described above, and an attempt to pass the IOL through the cartridge is made. In certain tests, the IOL is maintained, or dwells, in the load chamber and/or in the injection tube for a period of time before the IOL is passed out of the injection tube. The amount of force needed to pass the IOL through the cartridge is noted. Dwelling of the IOL in the load chamber and/or injection tube tends to squeeze out some of the aqueous hyaluronate solution from underneath the IOL. This increases the frictional force between the IOL and the interior surface of the cartridge and requires more force to pass the IOL.

A number of the cartridges are tested after being soaked in saline for four (4) days, and then dried.

Six (6) additional cartridges similar to those described above are tested in a similar manner except that the cartridges are not treated to form a coating of PVP covalently bonded at the interior walls of the cartridges.

The results of these tests are as follows:

these tests the distal ends of the injection tube of the cartridges are suitable for insertion into an approximately 2.6 mm incision. This is smaller than the distal ends of injection tubes of cartridges which are currently used commercially.

Thus, the present cartridges with covalently bonded lubricity enhancing components at the interior surfaces are particularly effective in assisting facilitating the passage of IOLs with optics that exhibit relatively large friction against the cartridges and/or of IOLs through a smaller incision, that is about 2.8 mm and more preferably less than 2.8 mm, into an eye.

EXAMPLE 2

Three (3) cartridges, having a structure similar to that of the body of IOL inserter 10, made of PD701NW polypropylene (Himont USA Inc.) are selected for testing. Each of these cartridges is treated with 4-azido-2-nitrophenyl polyethylene glycol (hereinafter A-PEG). This material, A-PEG, is made using polyethylene glycol having a nominal molecular weight of 1000 using the procedure outlined in Example 2 of Guire U.S. Pat. No. 4,979,959. A solution including A-PEG is allowed to adsorb onto the interior surfaces of the cartridges at room temperature in the dark, for approximately 3 hours. The A-PEG is then covalently bonded to the

| Cartridge ID | IOL Diopter Power | Dwell Time In Load Chamber, Minutes | Force Needed to Pass IOL Out of Load Chamber | Dwell Time In Injection Tube - Minutes | Force Needed to Pass IOL Out of Injection Tube | IOL is Passed Through Cartridge |
|---|---|---|---|---|---|---|
| 1 (not soaked) | 17 | 0 | Low | 0 | Low | Yes |
| 2 (not soaked) | 18 | 1 | Low | 3 | Low | Yes |
| 3 (not soaked) | 18 | 2 | Low | 5 | Low | Yes |
| 4 (not soaked) | 18 | 2 | Low | 5 | Low | Yes |
| 5 (not soaked) | 18 | 3 | Low | 5 | Low | Yes |
| 6 (4-day soaked) | 21 | 0 | Low | 0 | Low | Yes |
| 7 (4-day soaked) | 21 | 1 | Low | 1 | Low | Yes |
| 8 (4-day soaked) | 21 | 1 | Low | 2 | Moderate | Yes |
| 9 (4-day soaked) | 21 | 1 | Low | 3 | Moderate | Yes |
| 10 (4-day soaked) | 21 | 1 | Low | 3 | Moderate | Yes |
| 11 (Untreated) | 20 | 0 | (1) | 0 | (1) | No |
| 12 (Untreated) | 20 | 0 | (1) | 0 | (1) | No |
| 13 (Untreated) | 20 | 0 | (1) | 0 | (1) | No |
| 14 (Untreated) | 20 | 0 | (1) | 0 | (1) | No |
| 15 (Untreated) | 20 | 0 | (1) | 0 | (1) | No |
| 16 (Untreated) | 20 | 0 | (1) | 0 | (1) | No |

(1) The IOL cannot pass through the injection tube. The amount of force that is applied is sufficiently high so as to result in the lens being torn and/or the rod of the hand piece bypassing the IOL in the load chamber or injection tube.

Further, additional treated cartridges similar to those described above are tested in a similar manner except that no visco elastic agent or BSS is used. In each of these tests, it is found that the IOL cannot be passed out of the injection tube.

The above results clearly indicate that the present treated cartridges, including a covalently bonded lubricity enhancing component at the interior surface, are very effective in facilitating the passage of an IOL when used in combination with a liquid component, such as an aqueous solution of sodium hyaluronate. This is quite surprising since using the treated cartridge alone or the liquid component together with an untreated cartridge is ineffective to pass an IOL through the cartridge.

It is important to note that the IOLs employed in these tests include optics which exhibit relatively large friction against the cartridges, and are, relatively speaking, more difficult to pass through inserters than IOLs with optics which exhibit less friction against the cartridges. Also, in cartridge by photolysis. After photolysis, the cartridges are soaked with normal saline to remove unbound material.

The performance of the cartridges is determined by the number of three piece IOLs (such as an IOL sold under the trademark SI-30NB by Allergan Medical Optics) can be passed through the cartridge before either the cartridge or an IOL breaks. As a comparison, three (3) untreated, similarly structured cartridges are also tested.

Each of these tests is conducted as follows. With the load chamber, in the open position, about 0.02 to 0.2 ml of a commercially available aqueous balanced salt solution (BSS) is injected into the injection tube and along the bottom of both sides of the troughs formed by the first and second wings. The three-piece IOL is placed, anterior side up, between the first and second wings. The first and second wings are then closed to approximately a 45° angle. Using rounded blade forceps the edges of the optic of the IOL are pushed down into the tube portion of the wings, and the center of the optic is pushed down as the wings are closed further. After closing the wings, the cartridge is placed in association with a hand piece, as described above, and an attempt to pass the IOL through the cartridge is made.

Results of these tests indicate that the treated cartridges, together with the BSS is effective to facilitate the passage of IOLs through the cartridges. Tests with the untreated cartridges indicate that such untreated cartridges when used in combination with BSS are substantially ineffective to facilitate the passage of the IOLs through the cartridges.

EXAMPLE 3

A series of tests are run using treated and untreated cartridges similar to those described in Example 2. These tests are conducted generally similarly to how the tests in Example 2 are conducted except that a visco elastic agent is used in place of BSS. The visco elastic agent used is an aqueous balanced salt solution of sodium hyaluronate sold by Allergan, Inc. under the trademark Vitrax.

The results of these tests are generally similar to the results reported in Example 2. That is, the use of the visco elastic agent above, like the BSS above, in an untreated cartridge is substantially ineffective to facilitate the passage of an IOL through the cartridge. Further, using the liquid visco elastic agent (like BSS) in combination or together with treated cartridges in accordance with the present invention enhances the ability to pass IOLs through the cartridges.

If the IOL is maintained in the presence of the visco elastic agent or BSS before an attempt is made to pass the IOL through the treated cartridge, the tests using the visco elastic agent indicate a somewhat greater enhancement in the ability of the cartridge to pass IOLs relative to the tests using BSS. No such enhancements are obtained in tests in which the IOL is maintained in an untreated cartridge (for example, for more than one (1) minute) in the presence of either BSS or the visco elastic agent. In other words, the untreated cartridge is ineffective to facilitate the passage of an IOL through the cartridge whether BSS or the visco elastic agent is used and whether the IOL is maintained in the cartridge for a period of time or not.

The results of the Examples demonstrate that the treated cartridges in accordance with the present invention in combination with BSS or a visco elastic agent enhance the ability of the cartridge to pass IOLs. The enhanced lubricity of these treated cartridges provides enhanced control, and preferably allows reduced force to be used, in passing an IOL, relative to the control provided and force needed in passing an IOL through an untreated cartridge used in combination with BSS or a visco elastic agent. This enhanced control and reduced force requirement result in advantageously reducing the risk of harming the cartridge (inserter) and/or the IOL by passing an IOL through the cartridge.

These results are highly unexpected, particularly since the BSS or a visco elastic agent or treated cartridges when used alone are substantially ineffective to facilitate the passage of IOLs with optics which exhibit relatively large friction against the cartridges and/or to facilitate the passage of IOLs through very small cartridges, as described above.

It is important that the covalently bonded lubricity enhancing component be located at the interior wall of the cartridge and that the IOL is passed through the interior of the cartridge. Thus, this invention is clearly distinguished from catheters with lubricants on the outer surface thereof. Such catheters are designed to be passed into the body, for example through tissue, rather than having objects, like IOLs, pass through hollow interior spaces. The fact that such catheters do not require liquid materials to facilitate passage into the body is but one clear indication that the present IOL inserters, which do employ liquid materials such as BSS and visco elastic agents, are different from, and not suggested by, such catheters.

While this invention has been described with respect of various specific examples and embodiments, it is to be understood that the invention is not limited thereto and that it can be variously practiced within the scope of the following claims.

What is claimed is:

1. An apparatus for inserting an intraocular lens through a small incision into an eye comprising:
    a hollow tube including an interior wall defining a hollow space through which an intraocular lens may be passed and an outlet through which said intraocular lens may be passed from said hollow space into an eye; and
    a lubricity enhancing component covalently bonded to said hollow tube at said interior wall in an amount effective to at least assist in facilitating the passage of said intraocular lens through said hollow space.

2. The apparatus of claim 1 wherein said lubricity enhancing component is effective to reduce the force needed to pass said intraocular lens through said hollow space relative to the force needed to pass an identical intraocular lens through the hollow space of a similar apparatus without said lubricity enhancing component.

3. The apparatus of claim 1 wherein said hollow tube is made of a polymeric material.

4. The apparatus of claim 1 wherein said hollow tube is made of polypropylene.

5. The apparatus of claim 1 wherein said lubricity enhancing component is selected from the group consisting of hydrophilic components, oleophilic components and mixtures thereof.

6. The apparatus of claim 1 wherein said hollow tube is sized to pass said intraocular lens into the eye through an incision no larger than 3.5 mm.

7. The apparatus of claim 1 wherein said hollow tube is sized to pass said intraocular lens into the eye through an incision no larger than 3.0 mm.

8. The apparatus of claim 1 wherein said hollow tube is sized to pass said intraocular lens into the eye through an incision of less than 2.8 mm in size.

9. The apparatus of claim 1 which further comprises a loading portion coupled to said hollow tube and sized and adapted to receive an intraocular lens for passage into said hollow space.

10. The apparatus of claim 9 wherein said lubricity enhancing component is covalently bonded to said loading portion in an amount effective to at least assist in facilitating the passage of said intraocular lens into said hollow space.

11. An apparatus for inserting an intraocular lens through a small incision into an eye comprising:
    a loading portion sized and adapted to receive an intraocular lens and to hold said intraocular lens in a folded state;
    a hollow tube including an interior wall defining a hollow space into which said intraocular lens in a folded state may be passed and an outlet through which said intraocular lens in a folded state may be passed from said hollow space into an eye; and
    a lubricity enhancing component covalently bonded to said hollow tube at said interior wall in an amount effective to at least assist in facilitating the passage of said intraocular lens in a folded state through said hollow space.

12. The apparatus of claim 11 wherein said hollow tube is made of a polymeric component, and said lubricity enhancing component is selected from the group consisting of hydrophilic components, oleophilic components and mixtures thereof.

13. The apparatus of claim 11 wherein said hollow tube is sized to pass said intraocular lens into the eye through an incision no larger than 3.5 mm.

14. The apparatus of claim 11 wherein said loading portion is sized and adapted to fold an intraocular lens into a folded state.

15. The apparatus of claim 11 wherein said lubricity enhancing component is covalently bonded to said loading portion in an amount effective to at least assist in facilitating the passage of said intraocular lens in a folded state into said hollow space.

16. A method for inserting an intraocular lens into an eye comprising:

placing an outlet of a hollow tube in or in proximity to an incision in an eye, said hollow tube including an interior wall defining a hollow space containing an intraocular lens in a folded state and an effective amount of a liquid component, and a lubricity enhancing component covalently bonded to said hollow tube at said interior wall, said liquid component and said lubricity enhancing component together being present in an amount effective to facilitate passing said intraocular lens in a folded state through said hollow space; and passing said intraocular lens from said hollow space through said outlet into said eye.

17. The method of claim 16 wherein said lubricity enhancing component is effective to reduce the force needed to pass said intraocular lens in a folded state through said hollow space relative to the force needed to pass an identical intraocular lens in a folded state through the hollow space of a similar apparatus without said lubricity enhancing component.

18. The method of claim 16 wherein said hollow tube is made of a polymeric material and said intraocular lens comprises an optic including a silicone polymeric material.

19. The method of claim 16 wherein said lubricity enhancing component is selected from the group consisting of hydrophilic components, oleophilic components and mixtures thereof and said hollow tube is sized to pass said intraocular lens into the eye through an incision no larger than 3.2 mm.

20. The method of claim 16 wherein said hollow tube is sized to pass said intraocular lens into the eye through an incision less than 2.8 mm in size.

21. The method of claim 16 wherein said liquid component is selected from the group consisting of liquid aqueous salt solutions, liquid aqueous media containing visco elastic components and mixtures thereof.

* * * * *